United States Patent [19]

Stegelmeier et al.

[11] Patent Number: 4,659,732

[45] Date of Patent: Apr. 21, 1987

[54] LIPOXYGENASE INHIBITING 1-ARYLALKYL-, 1-ARYLTHIO-, AND 1-ARYLOXYPYRAZOLE-4,5-DIONES

[75] Inventors: Hartmut Stegelmeier, Hilden; Volker Fiedler, Leverkusen, both of Fed. Rep. of Germany; Mithat Mardin, Madison, Conn.; Dieter Mayer, Werne, Fed. Rep. of Germany; Elisabeth Perzborn, Wuppertal, Fed. Rep. of Germany; Friedel Seuter, Wuppertal, Fed. Rep. of Germany

[73] Assignee: Bayer Aktiengesellschaft, Leverkusen, Fed. Rep. of Germany

[21] Appl. No.: 769,928

[22] Filed: Aug. 27, 1985

[30] Foreign Application Priority Data

Aug. 31, 1984 [DE] Fed. Rep. of Germany ....... 3432062

[51] Int. Cl.[4] ................... A61K 31/415; C07D 231/28
[52] U.S. Cl. ..................................... 514/404; 548/365
[58] Field of Search ........................ 548/365; 514/404

[56] References Cited

U.S. PATENT DOCUMENTS 2,510,696  6/1950  Hunter et al. ..................... 514/404
4,000,294 12/1976  Moller et al. ..................... 514/404

FOREIGN PATENT DOCUMENTS 1181057 11/1964 Fed. Rep. of Germany ...... 514/404
2554701  6/1977 Fed. Rep. of Germany ...... 514/404

OTHER PUBLICATIONS

*Stedman's Medical Dictionary*, 23rd edit., 1976, pp. 1230–1231.
Anästh. Intensivther, Notfallmed. 17(1982) "Neue Aspekete zur Schocklunge" G. Schalag, H. Redl, p. 86.
Studies on the Pathogenesis of the Adult Respiratory Distress Syndrome J. Clin. Invest., The Amer. Soc. for Clin. Invest., Inc., vol. 69, 3/82, pp. 543–544.

*Primary Examiner*—Richard A. Schwartz
*Assistant Examiner*—Kurt G. Briscoe
*Attorney, Agent, or Firm*—Sprung Horn Kramer & Woods

[57] ABSTRACT

Combating diseases of the respiratory tract, inflammations, rheumatism, thromboembolic diseases, ischaemias and infarcts, cardiac arrhythmias and arteriosclerosis with pyrazolediones of the formula

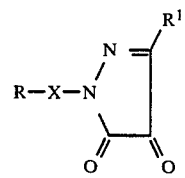

wherein
R represents an aryl or heteroaryl radical which has 6 to 12 C atoms and optionally contains 1 to 3 identical or different substituents from the group comprising halogen, trifluoromethyl, alkyl, alkenyl, alkoxy, alkylamino, cyano, trifluoromethoxy, nitro, hydroxyl, $SO_n$-alkyl (n=0 to 2) or $SO_n$-trifluoromethyl) n=0 to 2), alkyl, alkenyl and alkoxy each having up to 4 C atoms,
$R^1$ represents hydrogen or a hydrocarbon radical which has 1 to 18 C atoms and optionally contains a hydroxyl, ether, ester or carboxyl group and optionally contains 1 to 3 halogen atoms, and X represents one of the groups $-CH_2-CH_2-CH_2-$, $-O-CH_2-CH_2-$, $-S-CH_2-CH_2-$, $-CH_2-CH_2-$, $-CH_2-$ or

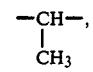

the oxygen or sulphur atom being bonded to the radical R.

10 Claims, No Drawings

LIPOXYGENASE INHIBITING 1-ARYLALKYL-, 1-ARYLTHIO-, AND 1-ARYLOXYPYRAZOLE-4,5-DIONES

The invention relates to pyrazoledione derivatives, processes for their preparation, their use in the prophylaxis and therapy of diseases of the respiratory tract, inflammations, rheumatism, thromboembolic diseases, ischaemias and infarcts, cardiac arrhythmias and arteriosclerosis, and mixtures of substances or medicaments which contain such pyrazoledione derivatives.

Known lipoxygenase inhibitors, such as nordihydroguaretic acid, 3-amino-1-(3-trifluoromethylphenyl)-2-pyrazoline, phenidone and 5,8,11,14-eicosatetraenoic acid, act as cyclooxygenase inhibitors either simultaneously or only at very high concentrations. The inhibition of the enzyme cyclooxygenase of the arachidonic acid metabolism leads to global inhibition of prostaglandin synthesis and in general to stimulation of the lipoxygenase pathway, which may result in gastrotoxicity and proinflammatory and asthmatic effects, as well as a greater tendency to thrombosis and arteriosclerosis.

Furthermore, known lipoxygenase inhibitors, such as 3-amino-1-(m-trifluoromethylphenyl)-2-pyrazoline, have toxic side effects when administered systemically (for example orally). There is therefore a need for more effective compounds having a more selective action profile without side effects.

It has now been found that certain 1-substituted pyrazole-4,5-dione derivatives act as inhibitors (stimulants) of enzymatic reactions within the arachidonic acid metabolism.

The invention relates to pyrazoledione derivatives of the formula

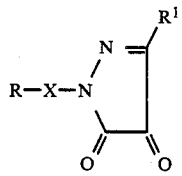

(I)

wherein

R represents an aryl or heteroaryl radical which has 6 to 12 C atoms and optionally contains 1 to 3 identical or different substituents from the group comprising halogen, trifluoromethyl, alkyl, alkenyl, alkoxy, alkylamino, cyano, trifluoromethoxy, nitro, hydroxyl, $SO_n$-alkyl (n=0 to 2) or $SO_n$-trifluoromethyl (n=0 to 2), alkyl, alkenyl and alkoxy each being understood as meaning radicals having 1 to 4 C atoms, $R^1$ represents hydrogen or a hydrocarbon radical which has 1 to 18, preferably 1 to 8, C atoms and optionally contains a hydroxyl, ether, ester or carboxyl group and optionally contains 1 to 3 halogen atoms, and X represents one of the groups —CH$_2$—CH$_2$—CH$_2$—, —O—CH$_2$—CH$_2$—, —S—CH$_2$—CH$_2$—, —CH$_2$—CH$_2$—, —CH$_2$— or

—CH—,
 |
 CH$_3$ the oxygen or sulphur atom being bonded to the radical R.

Compounds which are preferred according to the invention are those of the general formula (I) in which R represents an optionally substituted naphthyl, diphenyl or phenyl radical, particularly preferably a naphthyl or diphenyl radical, in particular α- or β-naphthyl. Preferably, these radicals carry 0, 1 or 2 substituents, in particular Br or Cl. Bromonaphthyl radicals are particularly preferred.

Other compounds which are preferred according to the invention are those of the general formula (I) in which $R^1$ represents a phenyl, benzyl or cyclohexyl radical or an aliphatic hydrocarbon radical, preferably a radical which has 1 to 4 C atoms and optionally contains a hydroxyl, ether or ester group, and $R^1$ particularly preferably represents an optionally branched $C_1$-$C_4$-alkyl group.

Finally, other compounds which are preferred according to the invention are those in which X represents —O—CH$_2$—CH$_2$—, —S—CH$_2$—CH$_2$—, —CH$_2$—CH$_2$—, —CH$_2$—CH$_2$—CH$_2$— or —CH—,
                          |
                          CH$_3$ in particular —O—CH$_2$—CH$_2$—, —CH$_2$—CH$_2$—CH$_2$— or —CH—.
                          |
                          CH$_3$ The pyrazoledione derivatives used according to the invention are suitable for the prevention and treatment of diseases of the respiratory tract, such as allergies-/asthma, bronchitis, emphysema, shock lung, pulmonary hypertension, inflammations/rheumatism and edemas, thromboses and thromboembolisms, ischaemias (peripheral, cardiac and cerebral disturbances of blood flow), cardiac and cerebral infarcts, arrhythmias, Angina pectoris and arteriosclerosis, in tissue transplantations, dermatoses, such as psoriasis, and metastases and for cytoprotection in the gastrointestinal tract.

The invention therefore also relates to the use of the pyrazoledione derivatives of the formula I stated above for the prophylactic and therapeutic treatment of the human or animal body.

The pyrazoledione derivatives to be employed according to the invention, of the general formula (I), can be prepared by the following processes.

Compounds of the formula (I) are obtained if (A) hydrazines of the formula

R—X—NH—NH$_2$   (II)

in which

R and X have the meaning given above, are reacted with β-keto acid derivatives of the formula

(III)

in which $R^1$ has the meaning given above and

Y represents a leaving radical, for example a hydroxyl, alkoxy, aralkoxy, amino or alkylamino radical, if appropriate in the presence of inert solvents and basic or acidic catalysts, such as alkali metal and alkaline earth metal hydroxides and carbonates or such as hydrohalic acids, sulphuric acid or sulphonic acids, at temperatures between 10° and 200° C., or (B) compounds of the formula $$R\text{—}X\text{—}A \quad \text{(IV)}$$

in which

R and X have the meaning given above and

A represents a leaving radical, such as halogen or a dialkyloxonium, dialkylsulphonium or trialkylammonium radical or an aryl- or trifluoromethylsulphonyl radical, are reacted with pyrazol-5-one derivatives of the formula

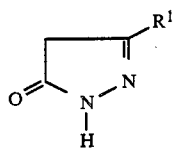

(V)

in which

R$^1$ has the meaning given above, if appropriate in the presence of inert solvents and inorganic or organic bases, such as alkali metal hydroxides, carbonates, alcoholates, hydrides or amides, at temperatures between 10° and 200° C., or (C) acetylenecarboxylic acid derivatives of the formula

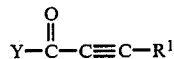

(VI)

in which

R$^1$ and Y have the meaning given above, are reacted with hydrazines of the above formula (II), if appropriate in the presence of inert solvents and inorganic or organic bases, at temperatures between 50° and 200° C., and the pyrazolinone derivatives obtained according to A-C are converted with nitrosobenzenes of the formula VII, in which R$^2$ and R$^3$ represent an aliphatic hydrocarbon radical, preferably having 1 to 4 C atoms,

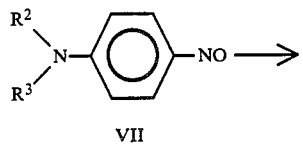

VII

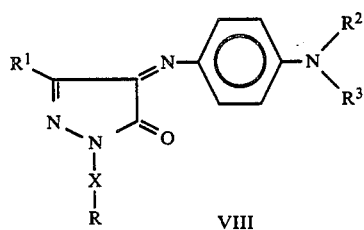

VIII by basic catalysis, to give the phenylimino derivatives of the formula VIII, which are hydrolyzed with dilute acid to give the pyrazoledione.

The biological action of the compounds prepared according to the invention was demonstrated by the following experiments:

(A) Lipoxygenase inhibition/cyclooxygenase inhibition/prostacyclin stimulation

1. Human PMN Leucocytes

The 5-lipoxygenase responsible for the biosynthesis of the leucotrienes B$_4$, C$_4$ and D$_4$ is inhibited selectively at low concentrations.

The human polymorphonuclear leucocytes metabolize the arachidonic acid to give 5-hydroxy-5,8,11,14-eicosatetraenoic acid (5-HETE) and leucotriene B$_4$ (5S,12R-dihydroxy-6 cis, 8,10-trans-14 cis-eicosatetraenoic acid). Inhibition of the liberation of 5-HETE and leucotriene B$_4$ from the leucocytes constitutes a measure of the lipoxygenase-inhibiting effect of the compounds according to the invention (see Table 1).

The test with the human leucocytes was carried out in accordance with Borgeat and Samuelsson (J. Biol. Chem. 254, 2643, 1979, and Proc. Natl. Acad. Sci. USA, 76, 2148, 1979).

The human PMN leucocytes (>95%) used in the present example were obtained from heparinized whole blood by dextran sedimentation and subsequent density gradient separation (Ficoll-Paque) (see A. Boyum, Scand. J. Immunol., 5, Suppl. 5, 9, 1976).

$2 \times 10^7$ cells/ml were suspended in Ca$^{2+}$-containing Dulbecco phosphate buffer and stimulated in the presence and absence of lipoxygenase inhibitors, with the calcium ionophore A 23 187. After 15 minutes, the lipoxygenase products were extracted from the acidified incubation medium and separated by means of HPLC.

2. $^3$H-arachidonic acid metabolism in human platelets (12-lipoxygenase activity and cyclooxygenase activity)

The lipoxygenase-inhibiting and cyclooxygenase-inhibiting properties of the compounds according to the invention were demonstrated analogously to the method due to Bailey et al., Journal of Biol. Chemistry 255, 5996, 1980, and in accordance with Blackwell and Flower, Prostaglandins 16, 417, 1978. In this test method, the metabolism of radiolabelled arachidonic acid in washed human platelets is employed. In this in vitro test, the radiolabelled metabolites are extracted from the reaction mixture and separated by thin-layer chromatography. The autoradiogram is evaluated in a thin layer scanner. Under these test conditions, the labelled metabolites are separated from the unreacted arachidonic acid and can then be evaluated quantitatively. The distribution of the radioactivity over the cyclooxygenase products thromboxane A$_2$ (determined as TXB$_2$) and 12-hydroxy-5,8,10-heptadecatrienoic acid (HHT) formed during the metabolic process, and the lipoxygenase product 12-hydroxy-5,8,11,14-eicosatetraenoic acid (12-HETE), under the effect of the inhibitors represents a measure of the inhibition of the enzymes.

3. Prostacyclin stimulation

The pyrazoledione derivatives to be used according to the invention also specifically stimulate the synthesis of prostacyclin (PGI$_2$). In contrast to thromboxane, which has a vasoconstrictor action and initiates platelet aggregation, PGI$_2$ is vasodilatory and inhibits platelet aggregation.

(a) In vitro stimulation in microsomes.

The specific PGI$_2$-stimulating action was demonstrated in vitro in a mixture of microsomes from sheeps' seminal vesicles (RVSM) and bovine aortas (BAM) (see F. Cottee et al., Prostaglandins, 14, 413, 1977). $^3$H-arachidonic acid was incubated with a mixture of RSVM and BAM for 10 minutes at 25° C. in the presence of the test substances. The reaction was stopped by acidification to pH 4.5. The fatty acid metabolites were extracted with ethyl acetate. The ethyl acetate was evaporated off under N$_2$, and the residue was taken up in CH$_3$OH/CHCl$_3$ (1:1) and the solution was applied onto TLC plastic films. Separation was effected by means of a mobile phase mixture consisting of ethylene acetate glacial acetic acid/isooctane/H$_2$O (110:20:50:10:organic phase) (P. Needleman et al., The Journal of Clinical Investigation 1978, 61, 839–849). The distribution of radioactivity was measured by means of a radio scanner.

(b) Ex vivo stimulation in aorta rings.

Aorta rings of rats pretreated with test substances are incubated for 10 minutes at 37° C. in tris buffer (PH 7.8). The prostacyclin which forms is converted to the stable 6-keto-PGF$_{1\alpha}$ and then determined radioimmunologically.

References:
McIntyre, D. E., Salzman, E. W., Thrombos. Haemostas. 46, 19, 1981.
Seuter, F. et al., 6th International Symposium on Arteriosclerosis, Abstr. 270, Berlin 1982.

(B) Stickiness of leucocytes

Surprisingly, it has also been found that the pyrazoledione derivatives to be used according to the invention reduce the stickiness of leucocytes, that is to say increase their rate of migration. The reduction in the leucocyte stickiness is also responsible for the decrease in ischaemic areas since, after treatment with the compounds to be used according to the invention, the leucocytes pass through the microcirculatory region of these areas without reducing the supply to the corresponding tissue by totally or temporarily closing small vessels or capillaries.

The number of leucocytes which pass through a certain section of a vessel serves as a simple model for measuring the stickiness of leucocytes (Bray, M. A. et al., Prostaglandins, 22, 213, 1981). The less sticky these cells are, the greater is the number of leucocytes counted.

Male Syrian golden hamsters (80–100 g) were anaesthetized with nembutal (i.p.; 60 mg/kg). After fixing a PE 10 catheter in the A.femoralis, the animal is laid on a Duling dissection stage (MVR 5, 423, 1973) and the right cheek pouch is drawn out by inserting a Q-tip. It is carefully drawn into that part of the stage which is intended for this purpose, and is stretched out and fixed. From the beginning of the preparation procedure, the prepared cheek pouch is rinsed over with 5 ml/minute of superfusate. The temperature of the solution is 36° C. While protecting the vessels, the upper layer of tissue is cut longitudinally and folded to the side. Under about 200 times magnification, an area of about 1 cm$^2$ of connective tissue is carefully exposed. The animal, together with the dissection stage, is placed on the microscope stage. A thermocouple is inserted into the left cheek pouch. The body temperature of the animal is monitored in this manner and maintained within +0.3° C. with the aid of an IR lamp (240 watt).

Measurement of the leucocyte stickiness is carried out under a magnification of about 500 times. A small vein (30–40 $\mu$m $\phi$) is selected in the exposed area. Over a certain section of this vessel, the number of leucocytes passing by per unit time (min.) is counted.

(C) Coronary thrombosis

A silver wire was implanted into the left coronary artery of anaesthetized dogs after the chest has been opened on the left side. A subcutaneous disc electrode completed the electric circuit. A direct anodal current was delivered to the artery for 6 hours (1). In untreated controls, complete vascular occlusion occurred after 3.2 hours as a result of platelet fibrin thrombus. This conclusion was drawn during the experiment from the cessation of coronary flow and ischemic changes in the electrocardiagram.

Benzothiazines were administered intraduodenally about 1 hour before the outset of stimulation with electrical current.

After the end of the experiment, the heart was removed and perfused with two solutions: Evans Blue via the aorta for marking the healthy, unaffected areas of the heart, and triphenyltetrazolium chloride for determining the perfusion area of the occluded artery (2). The infarct in the perfusion area of the occluded coronary artery was enclosed as an uncolored pale region and could be determined either by planimetry of the heart sections or by cutting them out from the myocardium.

(1) Romson J L, Haack D W, Lucchesi B R. Electrical induction of coronary artery thrombosis in the ambulatory canine: a model for in vivo evaluation of antithrombotic agents. Thromb. Res. 17, 841–853, 1980.
(2) Romson J L, Bush L R, Haack D W, Lucchesi B R. The beneficial effects of oral ibuprofen on coronary artery thrombosis and myocardial aschemia in the conscious dog. J. Pharmacol. Expl. Ther. 215, 271–278, 1980.

(D) Myocardial infarct and cardiac arrythmias

The actions of various pyrazoledione derivatives on the experimental myocardial infarct in the dog were investigated after acute ligature of a coronary artery. In pentobarbital-anaesthetised dogs, the proximal left anterior descending coronary artery (LAD) gradually occluded for 6 hours. The artery was not reperfused. One hour prior to ligature, the test compounds in 1% tyclose suspension were administered intraduodenally as a bolus. The same procedure was adopted for the controls, except that no active compound was administered. The size of the infarct and the area of perfusion of the LAD were determined biochemically by means of a dual perfusion method using Evans Blue and triphenyltetrazolium chloride. After the gradual ultimate LAD ligarure the 4H-1,4-benzothiazine substantially reduced the infarct size. This could be observed both with respect to the absolute infarct weight and the infarct size relative to the weight of the left ventricule. Initially, the blood pressure decreased as a result of the coronary ligature, and this led to a reflectory increase in the heart rate. Otherwise, no haemodynamic effects due to 4H-1,4-benzothiazine were observed. The compounds reduced the infarct-dependent increases in the electrocardigraphic ST segments of the peripheral electrocardiogram indicating reduced myocardial ischemia.

RESULTS (A 1-3) Lipoxygenase inhibition in human PMN's; (table 1), cyclooxygenase inhibition in platelets and prostacyclin stimulation in microsomes.

Surprisingly, the pyrazoledione derivatives to be used according to the invention selectively inhibit the 5-lipoxygenase responsible for the biosynthesis of the leucotrienes $B_4$, $C_4$ and $D_4$. The 12-lipoxygenase activity is not inhibited at these concentrations by the pyrazoledione derivatives to be used according to the invention.

Furthermore, the pyrazolone derivatives to be used according to the invention stimulate the synthesis of prostacyclin ($PGI_2$).

The cyclooxygenase is affected only at very high concentrations ($1 \times 10^{-5}$ g/ml), if at all.

(B) Stickiness of leucocytes; (table 2).

Surprisingly, it was also found that the pyrazoledione derivatives to be used according to the invention reduced the stickiness of leucocytes, that is to say increased their migration rate. This reduction in the stickiness of leucocytes is also responsible for the decrease in ischaemic areas since, after treatment with the pyrazolone derivatives to be used according to the invention, the leucocytes pass through the microcirculatory region of these areas without reducing the supply to the corresponding tissue as a result of total or temporary occlusion of small vessels or capillaries.

TABLE 1

| Inhibition of $LTB_4$ synthesis in human leucocytes | | | | |
|---|---|---|---|---|
| Substance | Inhibition (%) | | | |
| | 5 μg/ml | 1 μg/ml | 0.5 μg/ml | 0.1 μg/ml |
| 6 | 100 | 88 | 60 | 38 |
| 4 | 100 | 60 | 47 | 15 |
| 8 | 100 | 35 | 10 | — |
| 10 | 100 | 56 | 12 | — |
| 2 | — | 12 | — | — |
| 7 | 100 | 21 | 10 | — |
| 3 | 100 | 37 | 20 | 6 |
| 5 | 84 | 29 | 12 | — |
| 9 | 73 | 40 | — | — |
| 11 | 32 | 29 | — | — |
| 1 | 100 | 85 | 60 | 29 |

TABLE 2

| Inhibition of leucocyte stickiness | |
|---|---|
| Substance | Effect after administration of 1 mg/kg i.a. |
| 1 | inhibition |
| 4 | inhibition |
| 5 | no action |
| 8 | no action |
| 10 | inhibition |
| 2 | inhibition |
| 7 | inhibition |
| 11 | inhibition |
| 3 | no effect |
| 9 | no effect |
| 6 | no effect |

C-D) Thrombosis/ischaemia (table 3)

Furthermore, the pyrazoledione derivatives to be employed according to the invention surprisingly reduce the size of coronary thromboses and have a positive effect on cardiac arrythmias. These intended uses, according to the invention, of the pyrazoledione derivatives to be employed according to the invention are also not suggested by the indications described at the outset and disclosed in the prior art.

TABLE 3

| Method | N dogs | Dose | Effect |
|---|---|---|---|
| Reperfusion arrhythmia | 2 | 30 mg/kg id | 50% less than control animals |
| Coronary thrombosis | 4 | 30 mg/kg id | 40% smaller coronary thromboses |

The medicaments according to the present invention contain not only the pyrazoledione derivatives to be employed according to the invention but also pharmaceutically acceptable diluents or excipients. These are understood as meaning non-toxic substances which, after being mixed with the active compound, convert the latter to a form suitable for administration. The term preferably excludes water and organic solvents which are conventionally used in chemical synthesis and have a low molecular weight, except when other pharmaceutically required constituents are present, such as salts in the correct amounts, in order to produce an isotonic preparation, buffers, surface-active agents, colorants and flavorings and preservatives. Examples of suitable solid and liquid diluents and excipients are the following: water-containing buffers which can be rendered isotonic by the addition of glucose or salts; non-toxic organic solvents, such as paraffins, vegetable oils, alcohols and glycols; ground natural minerals (for example kaolins, aluminas, talc or chalk); synthetic powdered minerals (for example highly disperse silica or silicates); sugar; and aqueous suspensions of cellulose derivatives, for example methylhydroxyethylcellulose (tylose).

As a rule, the medicaments according to the invention contain 0.5 to 95% by weight, preferably 1 to 90% by weight, particularly preferably 5 to 50% by weight, of the pyrazoledione derivatives to be employed according to the invention.

Oral administration can be effected using solid and liquid dosage forms, such as powders, tablets, dragees, capsules, granules, suspensions, solutions and the like. If appropriate, the dosage units for oral administration can be microencapsulated in order to delay release or to extend it over a prolonged period, as, for example, by coating or embedding particulate material in polymers, wax or the like.

Parenteral administration can be effected using liquid dosage forms, such as sterile solutions and suspensions, which are intended for subcutaneous, intramuscular or intravenous injection. These are prepared by suspending or dissolving a measured amount of the active compound in a non-toxic liquid extender suitable for injection, such as an aqueous or oily medium, and sterilizing the suspension or solution. Stabilizers, preservatives and emulsifiers may also be added.

In humans, the daily dose, relative to the body weight, of the active compound is in general 0.01 to 50 mg/kg, preferably 0.1 to 10 mg/kg for parenteral administration, and in general 0.1 to 500 mg/kg, preferably 0.5 to 100 mg/kg, particularly preferably 1 to 50 mg/kg, for oral administration.

The dosage unit (tablet, capsule ampule, etc.) contains, as a rule, 1 to 100 mg, preferably 5 to 50 mg, particularly preferably 10 to 30 mg, of the pyrazoledione derivatives to be employed according to the invention.

EXAMPLE 1

3-Methyl-1-[2-(2-naphthyloxy)-ethyl]-2-pyrazole-4,5-dione 7.2 g (0.04 mol) of 4-nitroso-diethylaniline in 80 ml of ethanol and 10 ml of sodium carbonate solution were heated to the boil. A suspension of 10.6 g (0.04 mol) of nafazatrom and 180 ml of ethanol and 20 ml of sodium carbonate solution were added in portions, and the mixture was heated under reflux for 14 hours. Thereafter, it was evaporated to dryness, the residue was taken up in 600 ml of $CH_2Cl_2$, 400 ml of semi-concentrated $H_2SO_4$ were added and the mixture was stirred overnight at room temperature. After the organic phase had been separated off, it was washed with water and dried over $Na_2SO_4$. Stripping off the solvent in a rotary evaporator gives a red oily crude product which is crystallized from ethyl acetate/ether (1:1).

Yield: 2.8 g (24.8%); m.p. 119°–121° C.

The following substances of the general formula were prepared by the process described in Example 1:

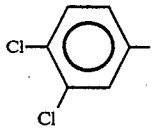

| Example | R | X | R¹ | m.p. (°C.) |
|---|---|---|---|---|
| 2 | $C_6H_5$— | —O—$CH_2CH_2$— | —$C(CH_3)_3$ | 79–81 |
| 3 |  | —CH—<br>\|<br>$CH_3$ | —$CH_2OCH_3$ | 84–85 |
| 4 | 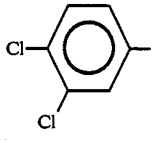 | —O—$CH_2CH_2$— | $CH_2OCH_3$ | 96–97 |
| 5 |  | —CH—<br>\|<br>$CH_3$ | —$CH_3$ | 60–62 |
| 6 | 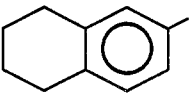 | —$OCH_2CH_2$ | —$CH_3$ | 91–92 |
| 7 | 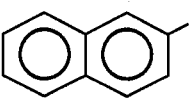 | —CH—<br>\|<br>$CH_3$ | —$CH_3$ | amorphous |
| 8 | 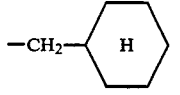 | —O—$CH_2CH_2$ | —$CH_2$—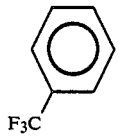 | 65–67 |
| 9 | 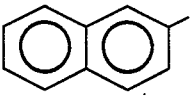 | —CH—<br>\|<br>$CH_3$ | —$CH_3$ | amorphous |
| 10 | 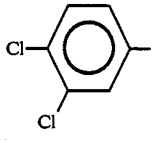 | —O—$CH_2CH_2$— | —$CH_2CH_2CH_3$ | 79–81 |

-continued

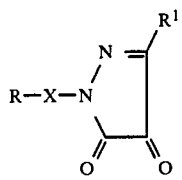

| Example | R | X | R¹ | m.p. (°C.) |
|---|---|---|---|---|
| 11 | (cyclohexyl) | —CH—<br>$\|$<br>CH₃ | —CH₃ | amorphous |

It will be understood that the specification and examples are illustrative but not limitative of the present invention and that other embodiments within the spirit and scope of the invention will suggest themselves to those skilled in the art.

We claim:

1. A pyrazoledione of the formula

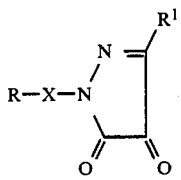

wherein

R represents a carbocyclic aryl which has 6 to 12 C atoms and is optionally substituted by 1 to 3 identical or different substituents from the group consisting of halogen, trifluoromethyl, alkyl, alkenyl, alkoxy, alkylamino, cyano, trifluoromethoxy, nitro, hydroxyl, SO$_n$-alkyl (n=0 to 2) or SO$_n$-trifluoromethyl (n=0 to 2), alkyl and alkoxy each having 1 to 4 C atoms and alkenyl having 2 to 4 C atoms, R¹ represents hydrogen or a hydrocarbon radical which has 1 to 18 C atoms and is optionally substituted by 1 to 3 halogen atoms and a hydroxyl, loweralkoxy, or carboxy group and X represents one of the groups —CH₂—CH₂—CH₂—, —O—CH₂—CH₂—, —S—CH₂—CH₂—, —CH₂—CH₂—, —CH₂— or

—CH—,
$\|$
CH₃ the oxygen or sulphur atom being bonded to the radical R.

2. A pyrazoledione according to claim 1, in which R represents a naphthyl, diphenyl or phenyl radical which is optionally substituted by 1 or 2 bromine or chlorine atoms.

3. A pyrazoledione according to claim 1, in which R¹ represents a phenyl, benzyl or cyclohexyl radical or an aliphatic hydrocarbon radical which is optionally substituted by a hydroxyl or loweralkoxy group.

4. A pyrazoledione according to claim 1, in which X represents —O—CH₂—CH₂—, —S—CH₂—CH₂—, —CH₂—CH₂—, —CH₂—CH₂—CH₂— or —CH—.
$\|$
CH₃

5. A pyrazoledione according to claim 1, in which R represents

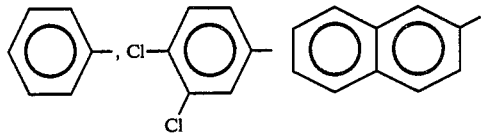

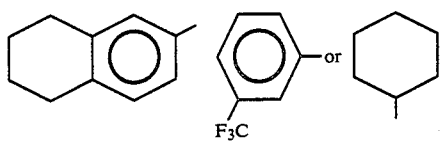

X represents a radical —O—CH₂—CH₂— or

—CH—
$\|$
CH₃ , and R¹ denotes —(CH₃)₃, —CH₂—O—CH₃, —CH₃,

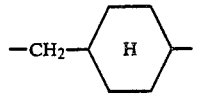

or —CH₂—CH₂—CH₃.

6. A pyrazoledione according to claim 1, wherein such compound is 3-methyl-1-[2-(2-naphthyloxy)-ethyl]-2-pyrazole-4,5-dione.

7. A pharmaceutical composition useful in the treatment of respiratory tract allergies, asthma, bronchitis, emphysema, shock lung, pulmonary hypertension, inflammations, inflammatory rheumatism, thromboembolic diseases, ischaemias and infarcts, cardiac arrhythmias, and arteriosclerosis, comprising an amount effective therefor of a pyrazoledione according to claim 1 in admixture with a diluent.

8. A unit dose of a composition according to claim 7 in the form of a tablet, capsule or ampule.

9. A method of treating a patient prophylactically or therapeutically for respiratory tract allergies, asthma, bronchitis, emphysema, shock lung, pulmonary hypertension, an inflammation, inflammatory rheumatism, thromboembolism, ischaemias and infarcts, cardiac arrhythmias, or arteriosclerosis, which comprises administering to such patient an amount effective therefor of a pyrazoledione according to claim 1.

10. The method according to claim 9, wherein such compound is 3-methyl-1-[2-(2-naphthyloxy)-ethyl]-2-pyrazole-4,5-dione.

* * * * *